United States Patent [19]

Shirai et al.

[11] Patent Number: 4,645,583
[45] Date of Patent: Feb. 24, 1987

[54] REFERENCE ELECTRODE

[75] Inventors: Tsuneo Shirai, 1-46-18 Chuo, Nakano-ku, Tokyo 164; Koji Suzuki, Kawasaki, both of Japan

[73] Assignees: Kuraray Co., Ltd.; Showa Denko Kabushiki Kaisha; Tsuneo Shirai, all of Tokyo, Japan

[21] Appl. No.: 836,403

[22] Filed: Mar. 5, 1986

[30] Foreign Application Priority Data

Sep. 9, 1985 [JP] Japan .................................. 60-199914

[51] Int. Cl.$^4$ ............................................ G01N 27/30
[52] U.S. Cl. ...................................... 204/435; 357/25
[58] Field of Search ................... 204/435, 418; 357/25

[56] References Cited

U.S. PATENT DOCUMENTS 4,269,682  5/1981  Yano et al. ..................... 357/25 X
4,592,824  6/1986  Smith et al. ......................... 204/416

Primary Examiner—G. L. Kaplan
Attorney, Agent, or Firm—Oblon, Fisher, Spivak, McClelland, & Maier

[57] ABSTRACT

A reference electrode in the form of a conductor, an ion sensitive field effect transistor or a liquid-membrane electrode kit, coated with a membrane of a high polymer which contains an arsonium borate. Since the reference electrode dispenses with a liquid junction region which has been required of a conventional liquid-junction type reference electrode, it has the following features. (A) It does not matter if the reference electrode is allowed to dry during storage. (B) The test solution is not contaminated by the internal solution. (C) Reduction in size of the reference electrode can be easily attained.

6 Claims, 10 Drawing Figures

REFERENCE ELECTRODE

BACKGROUND OF THE INVENTION

1. Field of the Invention

The present invention relates to a reference electrode which imparts a standard potential to a chemically sensitive electrode of potentiometric type.

2. Description of the Prior Art

Chemically sensitive electrodes are roughly classified into two types. A first type is the potentiometric electrode for measuring the concentration of a particular chemical substance in a test solution by making use of a potential gradient at the interface between the electrode and the solution. As those belonging to this type, there can be mentioned pH sensitive electrodes and ion sensitive electrodes which are sensitive to such ions as $Na^+$, $K^+$ and $Ca^{2+}$. A second type is the amperometric electrode which utilizes electric currents produced by oxidation-reduction reaction taking place on the electrode surface. As those belonging to this type, there can be mentioned oxygen electrodes and hydrogen peroxide electrodes. The potentiometric measuring system requires a reference electrode to be associated with a chemically sensitive electrode. A reference electrode is an electrode which is not sensitive to the various components in a test solution and which imparts a standard potential to a chemically sensitive electrode.

So-called liquid-junction type reference electrodes, such as calomel electrodes and silver-silver chloride electrodes, have heretofore been used as reference electrodes. As an example of a liquid-junction type reference electrode, the basic construction of a silver-silver chloride electrode is shown in FIG. 4. This silver-silver chloride electrode comprises a silver wire 1 having its surface chlorinated, said silver wire being received in a container 2 together with an internal solution 5 containing chloride ions of given concentration. The container 2 has a liquid-junction port 3 and an internal solution supply port 4. The liquid-junction port is provided for forming a liquid junction between the internal solution and the test solution, the liquid junction region being usually in the form of a pin hole, porous ceramic or the like. The potential at the silver-silver chloride wire changes with the chloride ion concentration of the internal solution, as indicated by equation (1).

$$E = E_o - \frac{RT}{F} \ln [Cl^-]. \tag{1}$$

where F stands for the Faraday constant, R the gas constant, T the absolute temperature, and $E_o$ a constant. The internal solution and the external test solution exchange, though gradually, through the liquid junction port and hence the chloride ion concentration of the internal solution changes. As a result, a fresh internal solution must be supplied at times through the supply port 4. Because of such basic construction, the liquid-junction type reference electrode has the following problems. (A) The electrode, particularly the liquid junction region, should not be allowed to dry during storage. Supply of internal solution and maintenance are troublesome. (B) It sometimes occurs that the internal solution leaks into the test solution through the liquid junction port, thus contaminating the test solution. (C) Reduction in size can hardly be attained.

On the other hand, a reference electrode FET (REFFET) based on an ion sensitive field effect transistor, which is a dry type reference electrode used in place of the liquid-junction type reference electrode, is known (Japanese Patent Publication No. 58-25221, Japanese Patent Application Laid-Open Specification Nos. 55-12480, 55-101852, 55-101853, 55-164348, and 56-100350, and U.S. Pat. No. 4,269,682). This reference electrode comprises an ion sensitive field effect transistor with its gate surface coated with a membrane of an ion insensitive hydrophobic organic high polymer, the potential at said reference electrode being determined by the potential gradient at the interface between the hydrophobic high polymer membrane and the solution. And in order for this reference electrode to function effectively as such, it is necessary that the potential not be influenced by the pH and total ion concentration of the solution. To this end, the following conditions should be satisfied. (1) Said high polymer membrane should be free of pinholes which would allow water and ions to pass therethrough. (2) Said high polymer membrane should have no or little, if any, amount of functional groups, such as OH, $NH_2$, $>C=O$ and $>NH$, which are capable of combining with metal ions to form complex compounds. (3) The thickness of said high polymer membrane should be within the range of 300 to 10,000 angstroms. However, without forming pinholes it would be difficult to form a 300 to 10,000-angstrom thick membrane on the surface of an ion sensitive field effect transistor. Further, if a hydrophobic high polymer membrane is kept in contact with air or water for a long time, a problem arises that the surface of the high polymer membrane is oxidized to form functional groups such as hydroxyl groups. As an example of REFFET of said system, there is disclosed (in Japanese Patent Publication No. 58-25221) a gate membrane formed of a polyvinyl chloride which is plasticized with dioctyl terephthalate (DOP). It has been reported, however, that such membrane is sensitive to quaternary ammonium ions, etc. Thus, there is a problem in using it as a gate membrane for REFFET (T. Higuchi et al., Analytical Chem., 1970, 1674). Due to aforesaid reasons REFFET has not yet been put into practical use.

SUMMARY OF THE INVENTION

We have conducted researches on a novel dry type reference electrode so as to solve the various problems of the aforesaid liquid-junction type reference electrode and REFFET.

An object of the invention is to provide a novel dry type reference electrode based on a new principle, which supersedes the aforesaid liquid-junction type reference electrode and REFFET.

This object is achieved by coating an electric conductor or the gate region of an ion sensitive field effect transistor (hereinafter referred to briefly as ISFET) with a membrane of a high polymer containing $(R_1 R_2 R_3 R_4 As)^+ (R_1' R_2' R_3' R_4' B)^-$ (hereinafter referred to briefly as AB, wherein $R_1$-$R_4$ and $R_1'$-$R_4'$ each stand for an alkyl group, a phenyl group or a phenyl group having a substituent) or by mounting said high polymer membrane on a conventional liquid membrane electrode kit (e.g., Philips model IS-561, Netherland, "Liquid-Membrane Electrode Kit" by Denki Kagaku Keiki Co. Ltd., Japan, etc.).

DESCRIPTION OF THE PREFERRED EMBODIMENTS

Figure 1:
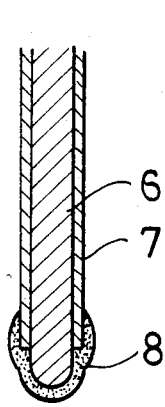
FIGS. 1, 2 and 3 are views showing the construction of a coated wire type reference electrode, an ISFET type reference electrode and a liquid-membrane electrode kit type reference electrode, respectively, according to the present invention.

As the AB to be added to a high polymer so as to obtain a reference electrode of the invention, there can be mentioned various arsonium borates obtained by suitably selecting the substituents $R_1$–$R_4$ and $R_1'$–$R_4'$. The aforesaid substituents are alkyl groups, phenyl groups and phenyl groups having substituents. Particularly, the alkyl groups are those having 3–15 carbon atoms, and the substituents in said phenyl groups are alkyl groups having 1–5 carbon atoms and such halogens as fluorine and chlorine. Groups which are capable of hydrogen bond, such as hydroxyl groups, carboxyl groups, amino groups and thiol groups, are not preferable for use as substituents in the phenyl groups. Examples of borate ions are tetraphenylborate ion, tetra-p-chlorophenylborate ion, tetra-p-methylphenylborate ion, tetradodecylborate ion and tetraoctylborate ion. Examples of arsonium ions are tetraphenylarsonium ion, tetra-p-chlorophenylarsonium ion, tetra-p-methylphenylarsonium ion, tetradodecylarsonium ion and tetraoctylarsonium ion. Examples of AB are salts which are formed by combination of said borate ions with arsonium ions, it being preferable that the mobilities of $A^+$ and $B^+$ be the same; thus, preferably, the substituents for the two are the same.

In the present invention, it is preferable from the standpoint of ease of availability that of said salts, tetraphenylarsonium tetraphenylborate (TPATPB) be used. Tetraphenylarsonium tetraphenylborate will be formed as a precipitate when equal molar amounts of tetraphenylarsonium chloride and sodium tetraphenylborate are mixed together in pure water. The precipitate is then extracted by chloroform or carbon tetrachloride, whereby TPATPB substantially free of such impurities as sodium and chloride ions can be obtained. In this connection it is to be noted that a reference electrode made of TPATPB which contains such impurities as sodium and chloride ions would have ion sensitivity.

Although there are no particular restrictions on high polymers to be used in the present invention, it is preferable that the high polymer be plasticized to the extent that the glass transition point be lower than the working temperature for the sensor so that arsonium and borate ions added are allowed to move in the high polymer. The plasticization may be either internal or external plasticization. Usually, for the plasticization of high polymers, a high polymer such as polyvinyl chloride, silicone rubber or cyclized rubber is mixed with a plasticizer (external plasticization). Such rubbers as silicone rubber and cyclized rubber may have their polymer composition adjusted so that they can be used without being mixed with a plasticizer (internal plasticization). As for polyvinyl chlorides, those having molecular weights of 10,000 to 1,000,000 are preferable. A preferable type of sililcone rubber is a room temperature curing one-liquid or two-liquid type silicone rubber known under the popular name of silicone RTV. As for cyclized rubber, cyclized polyisoprene and cyclized polybutadiene having molecular weights of 10,000 to 1,000,000 are preferable. Among preferable plasticizers are di(2-ethylhexyl) sebacate, dioctyl phthalate, dioctyl adipate, tricresyl phosphate and dibutyl phthalate. Electrode membranes are formed of a composition comprising a uniform mixture of 1–10 weight % AB, 10–70 weight % plasticizer and 30–90 weight % said high polymer. As the methods of forming such electrode membrane on a base electrode surface, besides one in which a membrane produced in advance by casting is applied thereto, there can be mentioned such direct membrane forming methods as dip coat method, molding method photoresist method and screen printing method. When silicone rubber or cyclized rubber is used as high polymer, curing takes place after membrane formation, inducing cross-linking in the high polymer membrane. The thickness of the electrode membrane is preferably in the range of 5 to 500 μm. If the thickness of the membrane is below the lower limit, the resulting mechanical strength would be insufficient and pinholes would easily form in the membrane. On the other hand, if the membrane thickness exceeds 500 μm, the potential at the reference electrode would tend to be unstable. The reference electrode of the invention is obtained by forming a high polymer membrane which has a thickness specified above. In this connection it is to be noted that whereas the aforesaid REFFET requires the formation of a 300–10,000 angstrom thick, pinhole free high polymer membrane, the formation of the reference electrode of the invention is much easier.

The reference electrode of the invention is characterized in that an electrode membrane is formed by using a high polymer composition which contains a particular arsonium borate, as described above. It is believed that such high polymer membrane plays the role of a salt bridge connecting the electrode surface and the external test solution, whereby the reference electrode of the invention functions effectively. Generally, the liquid potential between the salt bridge and the test solution is determined by Henderson's equation (P. Henderson, Z. Physik. Chem. 63, 325 (1908)). According to this equation, if the activity of the ions $X^+$ and $Y^-$ in the salt bridge is sufficiently higher than that of the same ions ($X^+$ and $Y^-$) in the external test solution and if the mobilities of the $X^+$ and $Y^-$ in the salt bridge are equal, then said liquid potential is zero. The ions $A^+$ and $B^-$ used in the present invention scarcely elute into water and the $A^+$ and $B^-$ are similar in size and molecular structure and their mobilities are substantially equal. Thus, it is believed that the liquid potential between the high polymer membrane containing AB and the external test solution is substantially zero.

The reference electrode of the invention will now be described with reference to the drawings.

Figure 2:
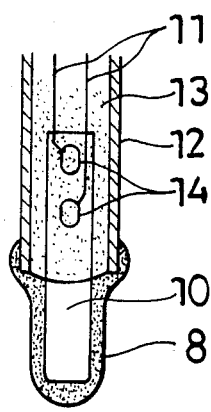
Figure 3:
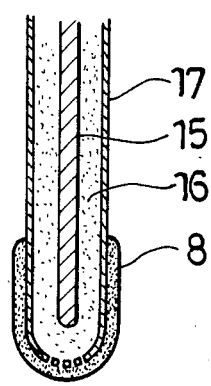
Figure 4:
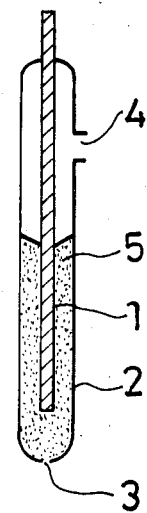
FIG. 4 is a view showing the basic construction of a conventional liquid-junction type reference electrode.

FIG. 1 shows a reference electrode using an electric conductor as a base. More particularly, said electrode comprises an electric conductor 6 in the form of a silver-silver chloride wire, a silver wire, a platinum wire or a gold wire, having its surface coated with an insulator 7, the front end thereof being coated with an AB-containing high polymer membrane 8; thus, it is a reference electrode of the so-called coated wire type. FIG. 2 shows a reference electrode having ISFET as a base. Thus, said electrode is produced by encapsulating the ISFET 10 and lead wires 11 in a tube 12, together with insulation resin 13, and forming an AB-containing high polymer membrane 8 around the gate region. The numeral 14 denotes electrodes. FIG. 3 shows a reference electrode based on a liquid-membrane electrode kit. Thus, said electrode is obtained by forming an AB-containing high polymer membrane 8 on a liquid-membrane electrode kit 17 which comprises a silver-silver chloride electrode 15 and an internal solution 16. In this manner, the reference electrode of the invention can be produced by coating the sensitive surface of a conventional chemically sensitive electrode with an AB-containing high polymer composition and forming said sensitive surface with a high polymer membrane. As is clear from the basic construction shown in FIGS. 1 and 2, the reference electrode of the invention is not of the liquid junction type. Particularly, the coated wire and ISFET type . reference electrodes do not require an internal solution; they are dry type reference electrodes in all respects. Although the liquid-membrane electrode kit type reference electrode shown in FIG. 3 uses an internal solution, it does not require a liquid junction region and hence there is no danger of leakage of liquid, nor is there the need of supplying additional internal solution. Thus, if the internal solution is sealed, the electrode can be regarded as a dry type reference electrode.

The reference electrode of the invention obtained in the manner described above has advantages. (A) It does not matter if the reference electrode of the invention dries during storage. As a matter of course, there is no need to supply additional internal solution. (B) There is no danger of the internal solution leaking into the test solution to contaminate the latter. (C) Reduction in size can be easily attained.

The present invention will now be described in more detail with reference to examples thereof, but it is not limited thereto.

EXAMPLE 1.

Equal molar amounts of tetraphenylarsonium chloride and sodium tetraphenylborate were mixed in pure water and the resulting TPATPB was extracted with chloroform. The chloroform was evaporated from the TPATPB-chloroform solution to provide TPATPB. 0.1 g of TPATPB thus obtained and 1.4 g of di(2-ethylhexyl) sebacate were dissolved in 10 ml of THF. On the other hand, 0.5 g of polyvinyl chloride (with a molecular weight of 25,000) was dissolved in 10 ml of THF and mixed with the aforesaid solution, thereby preparing a raw solution for forming an electrode membrane consisting of TPATPB, plasticizer, polyvinyl chloride and THF.

A 100-μm thick electrode membrane was produced from said electrode membrane forming raw solution by casting method, and said electrode membrane was attached to a liquid membrane electrode kit which was commercially available, thereby producing a reference electrode such as the one shown in FIG. 3. This will be referred to as the reference electrode Ⓐ. A silver-silver chloride wire was coated with said electrode membrane forming raw solution, and then the THF was evaporated; in this manner, a reference electrode such as the one shown in FIG. 1 was produced. This will be referred to as the reference electrode Ⓑ. Further, a platinum wire was coated with said electrode membrane forming raw solution to provide a reference electrode Ⓒ.

Figure 5:
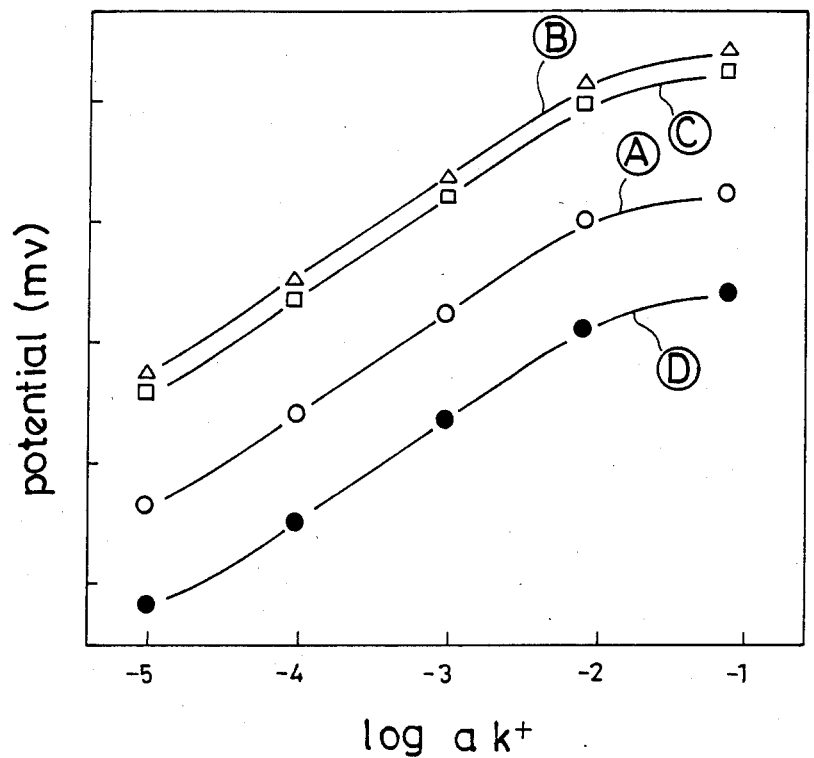
FIGS. 5, 6 and 7 show calibration curves for a potassium ion sensitive electrode, a chloride ion sensitive electrode and a pH sensitive electrode, respectively.

A potassium ion sensitive electrode using valinomycin was combined with the various reference electrodes to make calibration curves for potassium ions. The reference electrodes used were a conventional liquid-junction type reference electrode (double junction type) Ⓓ or the aforesaid reference electrode Ⓐ, Ⓑ or Ⓒ. The result is shown in FIG. 5. In the case where the reference electrodes Ⓐ, Ⓑ and Ⓒ are used, it is seen that the gradients and linear regions of the calibration curves are substantially the same as in the conventional liquid junction type reference electrode.

Figure 6:
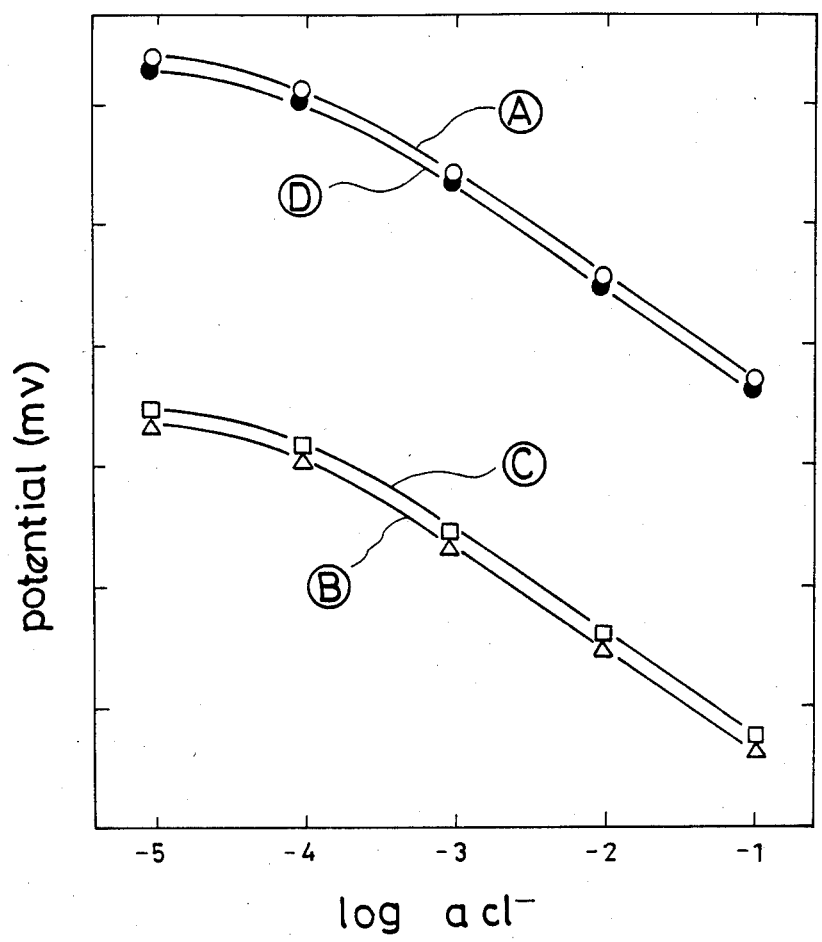

FIG. 6 shows calibration curves for a chloride ion sensitive electrode using trioctylmethylammonium chloride. In the case of chloride ions also, it is clear that concerning the gradient and linear region, the reference electrodes Ⓐ, Ⓑ and Ⓒ give the same results as the conventional reference electrode Ⓒ.

Figure 7:
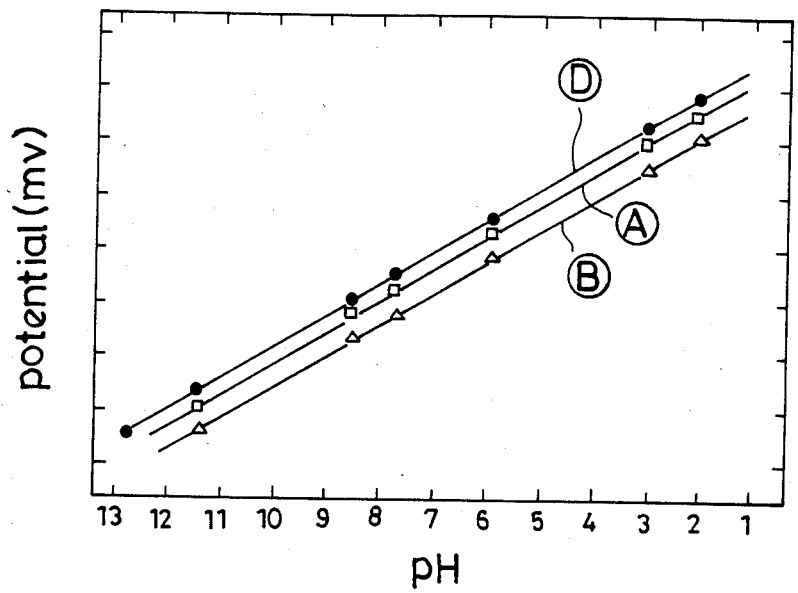

FIG. 7 shows calibration curves for hydrogen ions using a pH sensitive glass electrode. In this case also, it is clear that the reference electrodes Ⓐ and Ⓑ give substantially the same result as the conventional reference electrode Ⓓ.

EXAMPLE 2

Lead wires were soldered to the bonding pad for the drain and source of a pH sensitive ISFET disclosed in Japanese Patent Publication No. 57-43863 (U.S. Pat. No. 4,218,298) and the bonding pad and the lead wires were sealed in a nylon tube together with epoxy resin. The gate region of the ISFET exposed from the nylon tube was dip-coated with the same electrode membrane forming raw solution as that used in Example 1, thereby producing the FET reference electrode shown in FIG. 2.

Figure 8:
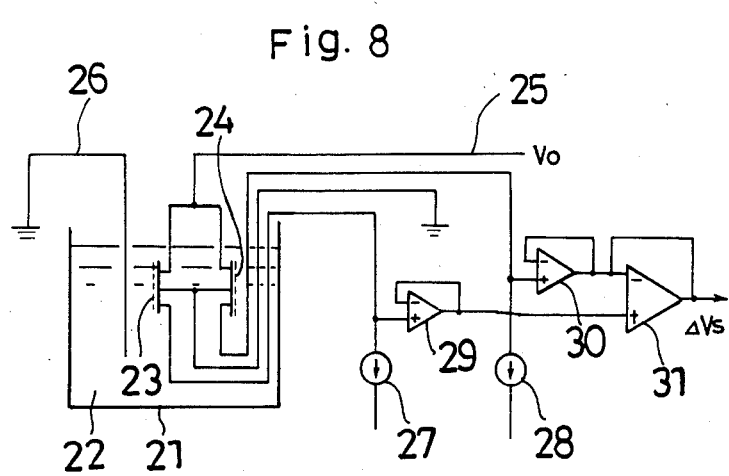
FIG. 8 is a diagram of a measuring circuit comprising a combination of a pH-ISFET and an FET reference electrode of the invention.

The aforesaid reference electrode and pH sensitive ISFET (pH-ISFET) were built in a differential circuit as shown in FIG. 8. In FIG. 8, the pH-ISFET 23 and FET reference electrode 24 were immersed in a test solution 22 in a container 21. A constant voltage source 25 was common to the pH-ISFET and FET reference electrode, $V_o$ being 4 volts. The numeral 26 denotes a pseudo reference electrode for maintaining the potential at the test solution at a constant value. The numerals 27 and 28 denote constant current devices whereby the currents flowing through the pH-ISFET and FET reference electrode are maintained at a constant value (30 μA, in this case). The source potentials at the pH-ISFET and FET reference electrode are amplified by impedance conversion circuits 29 and 30, respectively, and then the difference between the two is found by a differential circuit 31.

Figure 9:
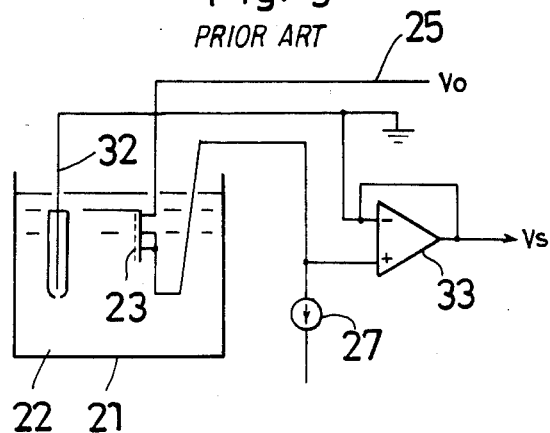
FIG. 9 is a diagram of a measuring circuit for actuating a pH-ISFET by using a conventional liquid-junction reference electrode.

FIG. 9 shows a circuit for measuring pH by using a conventional liquid junction type reference electrode and a pH sensitive ISFET. The pH-ISFET 23 and the liquid junction type reference electrode 32 are immersed in a test solution 22 in a container 21 and a voltage (4 volts) from a constant voltage source is applied to said pH-ISFET, a constant current device 27 providing a constant current (30 μA). The potential with respect to the liquid junction type reference electrode of the pH-ISFET is delivered at Vs by an impedance converter 33.

Figure 10:
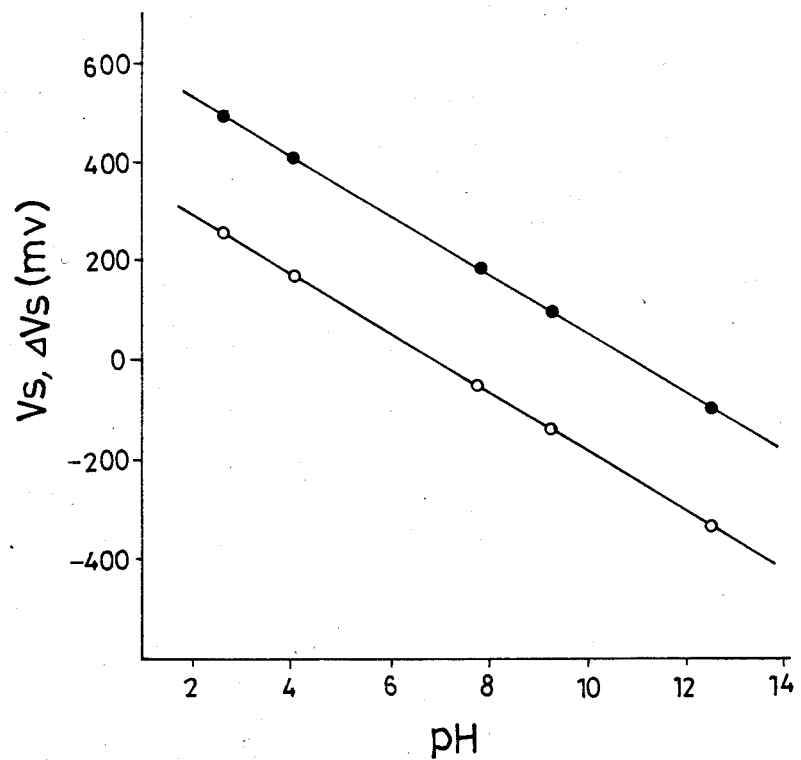
FIG. 10 shows calibration curves for pH sensitive electrodes obtained by the measuring methods shown in FIGS. 8 and 9.

The relation between the source potential of the pH-ISFET and the pH of the test solution was examined in the case of using the FET reference electrode as shown in FIG. 8 and the liquid junction type reference electrode as shown in FIG. 9. The result is shown in FIG. 10. In FIG. 10, black circles indicate the liquid junction reference electrode and white circles the FET reference electrode, it being clear that the lines provided have substantially the same gradient.

Obviously, numerous additional modifications and variations of the present invention are possible in light of the above teaching. It is therefore to be understood that within the scope of the appended claims, the invention may be practiced otherwise than as specifically described herein.

What is claimed is:

1. A reference electrode characterized in that it uses as an electrode membrane a membrane of a high polymer containing a salt which consists of a cation represented by the formula $(R_1 R_2 R_3 R_4 A_s)^+$ and an anion represented by the formula $(R_1' R_2' R_3' R_4' B)^-$ (wherein $R_1$, $R_2$, $R_3$, $R_4$, $R_1'$, $R_2'$, $R_3'$ and $R_4'$ each represent an alkyl group, a phenyl group or a phenyl group having a substituent).

2. A reference electrode as set forth in claim 1, wherein said salt is tetraphenylarsonium tetraphenylborate.

3. A reference electrode as set forth in claim 1, wherein the thickness of said high polymer membrane is 5–500 $\mu$m.

4. A reference electrode as set forth in claim 1, wherein the high polymer of said high polymer membrane is plasticized.

5. A reference electrode as set forth in claim 1, wherein said high polymer is plasticized polyvinyl chloride.

6. A reference electrode as set forth in claim 1, wherein the electrode coated with said electrode membrane is an ion sensitive field effect transistor.

* * * * *